United States Patent [19]

Salb

[11] Patent Number: 5,408,996
[45] Date of Patent: Apr. 25, 1995

[54] SYSTEM AND METHOD FOR LOCALIZATION OF MALIGNANT TISSUE

[76] Inventor: Jesse Salb, 10445 Wilshire Blvd., Los Angeles, Calif. 90024

[21] Appl. No.: 36,912

[22] Filed: Mar. 25, 1993

[51] Int. Cl.$^6$ ............................................. A61B 5/00
[52] U.S. Cl. .................... 128/633; 128/634; 128/665; 128/6
[58] Field of Search ............... 128/633, 634, 653.1, 128/665, 6; 364/413.13

[56] References Cited

U.S. PATENT DOCUMENTS

| | | | |
|---|---|---|---|
| 4,773,097 | 9/1988 | Suzaki et al. | 128/633 |
| 4,821,117 | 4/1989 | Sekiguchi | 128/6 |
| 5,001,054 | 3/1991 | Wagner | 128/637 |
| 5,078,150 | 1/1992 | Hara et al. | 128/665 |
| 5,092,331 | 3/1992 | Nakamura et al. | 128/665 |
| 5,146,923 | 9/1992 | Dhawan | 128/665 |

OTHER PUBLICATIONS

Kinsey et al., "Endoscopic system for simultaneous visual examination and electronic detection of fluorescence", Rev. Sci. Instr. 5(10), Oct. 1980, pp. 1403–1406.

*Primary Examiner*—Krista M. Pfaffle
*Attorney, Agent, or Firm*—Blakely, Sokoloff, Taylor & Zafman

[57] ABSTRACT

System and method for detection and localization of malignant tissue in situ during a medical procedure such as endoscopy or surgery. A fluorescent metabolic imaging agent, consisting of a carbohydrate analog coupled to a fluorophore in a manner such that the imaging agent accumulates in tissue in proportion to the glucose metabolic rate of the tissue, is systemically or locally injected into a patient before commencement of the endoscopic or surgical procedure. After a period of time during which the imaging agent accumulates in the body tissue, the tissue under examination in the endoscopic or surgical field of view is illuminated by a broadband light source filtered by an optical bandpass excitation filter to transmit light at the fluorescent excitation wavelength of the imaging agent. An optical bandpass emission filter filters the light emitted from the illuminated tissue to transmit light at the fluorescent emission wavelength of the imaging agent to a high-sensitivity cooled-CCD video camera. The CCD video camera acquires an image of the tissue, and a camera controller digitizes the analog video output signal of the camera and transfers the digitized data to a computer. The computer software reformats the data into a video frame, performs image processing algorithms on the video frame, and displays the frame on a video monitor as a color-coded image. Different colors in the color scale represent varying levels of glucose metabolism in different areas of the tissue under examination, and areas of malignant tissue are detectable by their characteristic hypermetabolism.

16 Claims, 3 Drawing Sheets

SYSTEM AND METHOD FOR LOCALIZATION OF MALIGNANT TISSUE

BACKGROUND OF THE INVENTION

This invention relates to medical imaging in general, and specifically to a system and method for the detection and localization in situ of hypermetabolic tissue, particularly malignant tissue, during medical procedures such as diagnostic endoscopy and oncological surgery.

Endoscopy entails the examination of an internal organ of the human body by insertion into the organ of two flexible fiber optic bundles contained within an outer flexible sheath. One fiber optic bundle illuminates the organ tissue and the second bundle conveys the image of the illuminated tissue back to the eye of the diagnostician or to a video camera. Historically, during endoscopic procedures the diagnostician, such as a gastroenterologist, has determined which areas of tissue are normal and which, if any, areas are abnormal and require biopsy solely by visual inspection of the endoscopic field of view.

Similarly, during surgical procedures the surgeon generally has determined which areas of tissue are normal and which areas are abnormal and therefore require resection (removal) primarily by visual examination of the tissue in the surgical field of view.

Differentiation of tissue solely by the criterion of visual appearance has several significant disadvantages. During an endoscopic procedure, for example, an area of malignant tissue may be too small to be observed even during careful visual inspection through the endoscope. The published literature in the field of gastroenterological endoscopy, for example, contains numerous references to cases in which an initial endoscopic examination failed to reveal the presence of malignant tissue, while subsequent examination after a period of a few months revealed detectable malignancy. The prevalence of this clinical phenomenon suggests that there is a minimum size threshold for visual detection of an area of malignancy, and that a technique which lowered the visual detection threshold would allow earlier detection of malignancy than is currently possible. In addition, current clinical practice is to biopsy all areas of tissue whose appearance is "borderline", i.e. neither definitely normal or abnormal. A method which would allow the unequivocal differentiation of normal from malignant tissue in situ would thus eliminate the need for numerous biopsies currently being performed.

Similarly, during oncological (tumor) surgery, differences between normal and malignant tissue are often not visually apparent in the surgical field of view, and tumors frequently do not have distinct boundaries. In addition, infiltration of tumor margins by malignant tissue is not visible to the unaided eye. Thus, a method which enhanced the oncological surgeon's ability to distinguish between normal and malignant tissue during the surgical procedure would allow more accurate and thorough resection of malignant tissue.

The need for more accurate detection and localization of malignant tissue in both endoscopy and surgery has led to the development of several techniques to supplement visual inspection.

For endoscopic applications, several attempts have been made to enhance the visual detection of malignant tissue using dyes which theoretically are absorbed at a higher rate by malignant tissue than by adjacent normal tissue. In practice, the disadvantage of this approach has been that the specificity of absorption of the dyes by malignant tissue is not sufficient to render the technique useful as a routine diagnostic tool.

For oncological surgery applications, a handheld probe has been developed which detects photon emission from tissue which has been treated preoperatively with radioactive tumor-specific antibody. The probe is manually swept over the general area of the tumor and those areas of high photon emission are assumed to be tumor tissue and are resected. The disadvantages of this approach are the time-consuming and laborious nature of the manual scanning procedure and the inability of the device to generate a coherent two-dimensional image of the surgical field of view.

It is thus obvious that the present state of the endoscopic and surgical arts do not offer a sufficiently practical and accurate method for endoscopic and surgical localization of malignant tissue in situ. An ideal system for endoscopic and surgical localization would combine a significant reduction in the size threshold for detection of very small, newly developing areas of malignant tissue, intrinsic visual registration of the image of the abnormal tissue on the image of the endoscopic or surgical field of view, ease of use in the diagnostic suite or the operating room, and rapid image acquisition, analysis, enhancement and display. Such a system would satisfy an important need in current diagnostic and surgical practice. It is the object of the present invention to provide a system and method fulfilling this need.

SUMMARY OF THE INVENTION

The present invention is a system and method to enhance the localization in situ of hypermetabolic tissue, particularly malignant tissue, during medical procedures such as diagnostic endoscopy and oncological surgery. The invention is based on the well established principle that normal and malignant tissue may be reliably differentiated by characteristically different rates of glucose metabolism. Specifically, virtually all types of malignant tissue metabolize glucose at significantly higher rates than corresponding normal tissue. In fact, there is essentially no overlap between the glucose metabolic rates of normal and malignant tissue.

The system and method described here exploits these reproducible, intrinsic differences in glucose metabolic rates between normal and malignant tissue to produce color-coded video images of the metabolic rates of different types of tissue visible in the field of view during an endoscopic or surgical procedure. The images are generated by first systemically or locally injecting the patient with a metabolic imaging agent before commencement of the endoscopic or surgical procedure. The metabolic imaging agent consists of a glucose analog coupled to a fluorophore, and accumulates in each type of tissue at a rate proportional to the glucose metabolic rate of that tissue. After the imaging agent accumulates throughout the body tissue for a measured period of time, the tissue under examination during the endoscopic or surgical procedure is illuminated by light at a wavelength which excites the fluorophore in the imaging agent and causes it to fluoresce. An image of the fluorescent-light-emitting tissue is captured by a high-sensitivity cooled-CCD video camera and the image is processed by a computer. The processed image is color-coded to represent the varying levels of glucose metabolism in different areas of the tissue under examination. The color-coded image is displayed on a video monitor, and areas of malignant tissue are detectable by their characteristic hypermetabolism.

Advantages of the present invention include the ability to perform in situ localization, higher spatial resolution than alternative imaging techniques, inherent image registration on the endoscopic or surgical field of view, the ability to generate the computed image in real time during the endoscopic or surgical procedure, convenience of use in the diagnostic suite or operating room, and the elimination of the need for radioactive isotopes or external radiation sources such as x-rays for the generation of images.

DETAILED DESCRIPTION OF THE INVENTION

Figure 1:
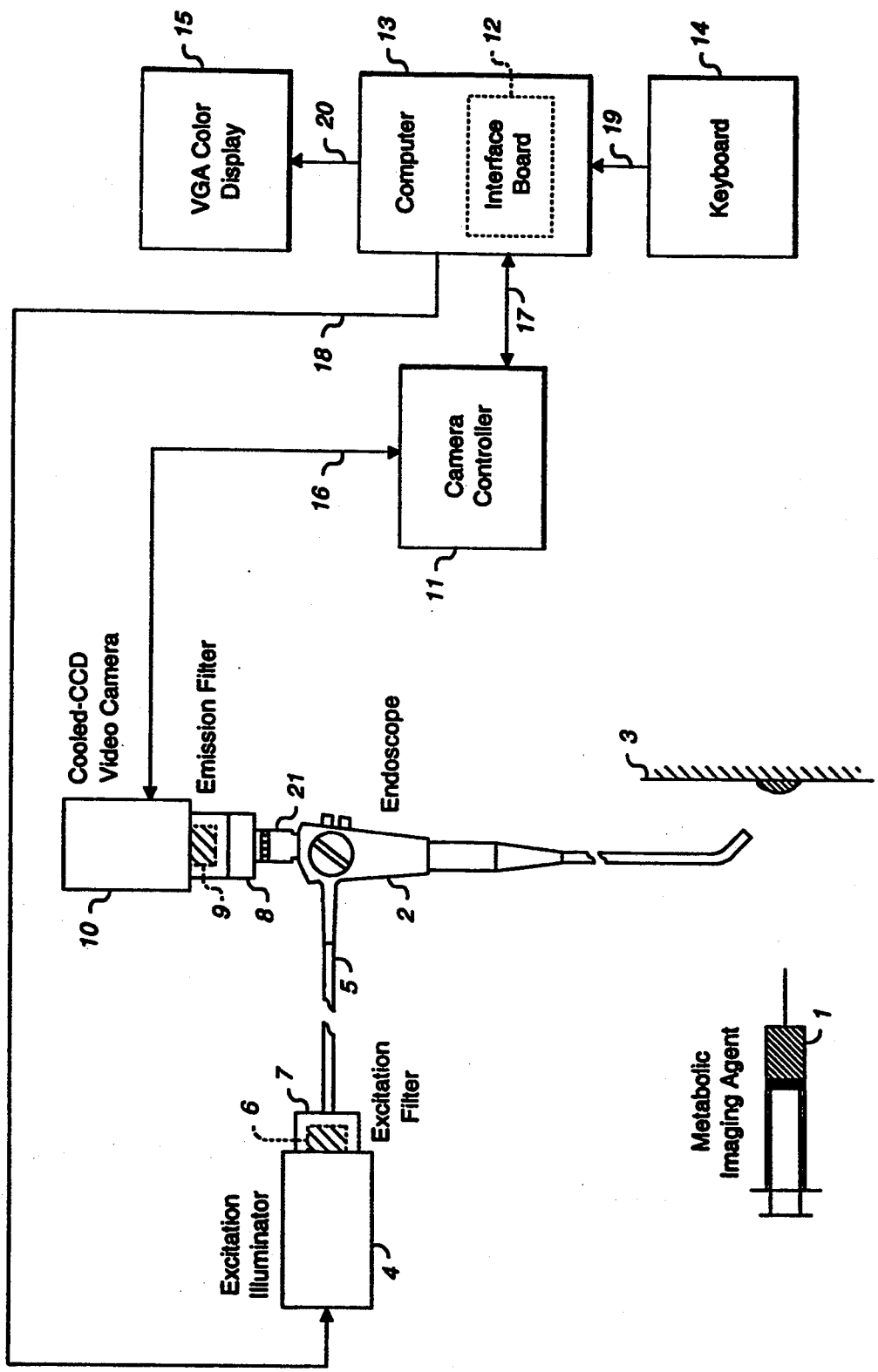
FIG. 1 is a block diagram of the system used in an endoscopic procedure.

FIG. 1 is a block diagram of the present invention used in an endoscopic procedure. The system comprises a fluorescent metabolic imaging agent 1 which is injected into the patient who will undergo the endoscopic procedure, an endoscope 2 to allow visual access to the tissue 3 in the body organ under examination, an excitation illuminator 4 for illuminating the tissue in the endoscopic field of view through endoscope light guide 5, an optical bandpass excitation filter 6 for filtering the broadband light output of the illuminator to transmit light at the excitation wavelength of the fluorescent metabolic imaging agent, an adapter device 7 for mounting the excitation filter and for coupling the filtered light output of the illuminator to the endoscope light guide, an adapter device 8 for coupling the optical image at the endoscope eyepiece 21 to an optical bandpass emission filter 9 to transmit light emitted from the illuminated tissue at the emission wavelength of the fluorescent metabolic imaging agent, a high-sensitivity cooled-CCD video camera 10 for acquiring images of the fluorescence-emitting tissue, a camera controller 11 for digitizing the analog video signal generated by the cooled-CCD video camera and for controlling the operation of the camera, an interface circuit board 12 for acquiring the digitized video data from the camera controller, a computer 13 and software for operation of the interface board and for formatting and image processing of the digitized video data, a keyboard 14 for user interaction with the computer, and a high-resolution VGA color display 15 for image and text display.

Figure 2:
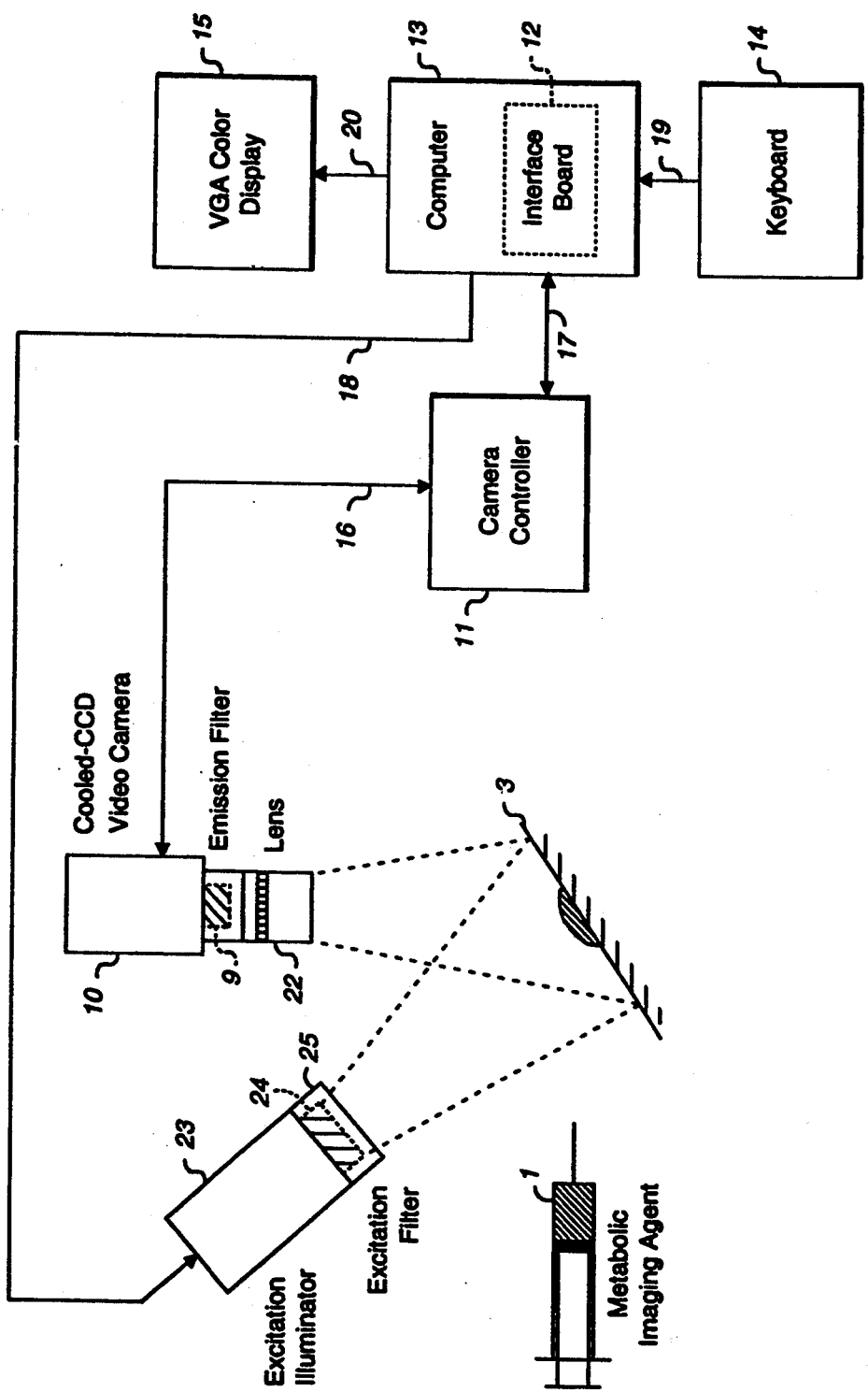
FIG. 2 is a block diagram of the system used in a surgical procedure.

FIG. 2 is a block diagram of the present invention used in a surgical procedure. The components of the system are similar to those used in the system for an endoscopic procedure depicted in FIG. 1. However, in the surgical procedure the endoscope 2 and adapter devices 7 and 8 are not used. The optical bandpass excitation filter 24 is mounted on the front of the illuminator 23 using adapter device 25. Also, a lens 22 is mounted on the CCD video camera 10. In addition, the camera 10 and the illuminator 23 are aimed directly onto the surgical field of view at the tissue 3 under examination. A detailed description of each section of the system is now presented.

I. Metabolic Imaging Agent

The metabolic imaging agent 1 is a glucose analog coupled to a fluorophore in a manner that allows transport of the imaging agent across the cell membrane and facilitates attachment of the agent to the substrate binding site of the hexokinase enzyme within the cell. Since the amount of hexokinase within a cell is proportional to the glucose metabolic rate of the cell, quantitation of this enzyme is a useful method for the detection of hypermetabolic tissue such as malignant tissue. It has been established that malignant tissue contains between 5 and 50 times the hexokinase of corresponding normal tissue.

The metabolic imaging agent may be a glucose analog such as glucosamine coupled to a fluorophore such as CY5 from Research Organics, Inc. The absorption wavelength maximum for CY5 is 652 nm with a useful range of 580 nm to 670 nm. The emission wavelength maximum for CY5 is 667 nm with a useful range of 650 nm to 685 nm. The relatively long emission wavelength of the fluorophore is selected specifically to avoid the autofluorescence noise of normal and malignant tissue, which is present at significant levels in the approximate wavelength range of 300 nm to 625 nm.

II. Excitation Illuminator

In an endoscopic application, the excitation illuminator 4 may be a xenon light source illuminator such as the Fujinon FLX-2000. The use of a xenon source with a highly regulated power supply provides a very stable light level output in the wavelength range of interest for fluorescent imaging applications. The FLX-2000 light output level may be electronically controlled from the computer through an analog voltage level transmitted over control line 18. The fiber optic illumination light guide 5 is connected to the excitation illuminator through a light source coupling adapter device 7. This adapter device also provides for mounting the excitation filter between the xenon light source and the proximal end of the fiber optic illumination guide.

In a surgical application, the excitation illuminator 23 may be a general purpose xenon-arc illuminator such as an Oriel 66006 arc lamp source powered by an Oriel 68805 regulated power supply. The 68805 power output level may be electronically controlled from the computer through an analog voltage level transmitted over control line 18. The excitation filter 24 is mounted on the front of the lamp housing using adapter device 25.

III. Excitation Filter

The optical excitation bandpass filter is positioned in the illuminating beam of the excitation illuminator to allow the transmission of light at the excitation wavelength of the metabolic imaging agent. In an endoscopic application, the filter 6 is positioned between the excitation illuminator 4 source and the endoscope light guide 5 using an adapter device 7. In a surgical application, the filter 24 is mounted in front of the excitation illuminator 23 source. The bandpass filter is produced using thin-film optical interference technology and may be an Omega Optical 590 DF 45 filter with a bandpass center frequency of 590 nm and with a 50% transmission bandwidth of 40 nm and very sharp cut-on and cut-off edges at 570 nm and 610 nm respectively.

IV. Endoscope

The endoscope 2 may be a typical fiberscope instrument of the type used in clinical applications, such as a Fujinon UGI-F7 endoscope. The UGI-F7 endoscope is classified as a gastroscope and is used for examination of the upper gastrointestinal tract. However, the system and method described here may also be used in any clinical situation in which an endoscopic procedure is performed, such as sigmoidoscopy or bronchoscopy, simply by using the appropriate type of endoscope.

The eyepiece 21 of the endoscope may be coupled to the CCD video camera using a camera adapter 8 such as the Fujinon MF-139. One side of the adapter is connected to the eyepiece of the endoscope, while the other side of the adapter mates with the Nikon lens mount on the CCD video camera 10.

V. Emission Filter

The optical emission bandpass filter 9 is positioned within the Nikon lens mount of the CCD video camera to allow the transmission of light emitted from the tissue under examination in the endoscopic or surgical procedure at the emission wavelength of the metabolic imaging agent. The bandpass filter is produced using thin-film optical interference technology and may be an Omega Optical 660 DF 32 filter with a bandpass center frequency of 660 nm and with a 50% transmission bandwidth of 40 nm and very sharp cut-on and cut-off edges at 640 nm and 680 nm respectively.

The bandpass cut-on edge of the emission filter is chosen to eliminate the autofluorescence noise of normal and malignant tissue, which is present at significant levels in the approximate wavelength range of 300 nm to 625 nm.

VI. Video Camera

A high-resolution, slow scan, cooled charge-coupled device (CCD) video camera 10, which may be a Princeton Instruments TE/CCD-512TK, is used to acquire images of the tissue under examination. The CCD used in this camera is organized as a 512×512 pixel device. The dynamic range of the camera is 17 bits, and the output scan rate of the CCD is 200 KHz, allowing the readout of an entire frame in 1.85 seconds.

In an endoscopic application, the CCD video camera 10 is coupled to the endoscope 2 through a commercially available endoscope camera adapter 8 which is mated with the Nikon lens mount on the camera. The camera lens mount is modified to allow the internal positioning of the optical emission bandpass filter 9 behind the lens mount and in front of the CCD. In a surgical application, a camera lens 22 is used which may be a Nikon 55mm F/2.8 macro lens. The lens is attached to the CCD video camera 10 using the camera lens mount. The use of a macro lens in a surgical application provides the ability to focus on the surgical field of view from close distances for high magnification when needed, while the telephoto perspective of the lens (when used with a video camera) allows routine imaging from a convenient distance in the operating room.

VII. Camera Controller

Operation of the CCD video camera is controlled by a camera controller module 11, which may be a Princeton Instruments Model ST-130 Universal Detector Controller. The controller controls the acquisition of a video frame from the CCD camera over digital control and analog data lines 16 and transfer of the frame to the computer over digital control and data lines 17 through the following sequence of operations. First, the controller sends a signal to the camera to open the camera shutter. The camera shutter is allowed to remain open for the predetermined duration of the exposure. The controller then sends a signal to the camera to close the camera shutter. The charge accumulated on the CCD is then read out, and the controller digitizes the analog signal from the camera with 16-bit resolution, with approximately 1 to 3 least-significant-bits of quantization noise, and at a rate of 200 KHz. After the entire contents of the CCD have been digitized, the controller transfers the array of 16-bit values to the interface board 12 installed in the computer 13 using a 16-bit parallel interface. The transfer rate of the parallel data is 400 Kb per second. As the interface board receives the digitized data it writes the data into main computer memory at high speed via a DMA transfer.

VIII. Computer

A 80486 50 MHz AT-compatible computer 13, which may be a Dolch V-P.A.C. 486-50 E EISA portable computer, is used for system control. The computer controls operation of camera interface controller board 12, acquisition of digitized video data from the interface board, and video image formatting, processing, and display. The computer is configured with 8 Mb of random-access memory, a 200 Mb hard disk drive, an internal VGA color display 15 with 640×480 pixel resolution and 256-color capability, and a Microsoft or compatible mouse (not shown). The computer is controlled by a keyboard 14 over digital data lines 19, and can transfer a 640×480 pixel resolution, 256-color capability video signal at a 60 Hz refresh rate to an optional external VGA color display over analog data lines 20.

IX. System Software

A commercial software package which runs under the MS-DOS operating system, such as the CSMA program from Princeton Instruments, is used to control the acquisition, image processing, display, and storage of the images captured by the CCD video camera 10. The program uses a Windows-type display format, with menu commands and video images displayed simultaneously on the same VGA color display 15.

The specific functions performed by the menu commands include camera setup parameters; image acquisition control; background noise subtraction; display of raw video frames; image processing algorithms such as lowpass filtering, highpass filtering and threshold operations; color scale modification using the output look-up-table (LUT); and hard disk image file storage and retrieval.

The program allows the creation of macro programs, which are sequences of individual menu commands which are automatically rerun each time the macro program is executed. This feature allows the complete automation of acquisition, processing, color-coding, display, and file storage of the video images described in this system.

X. Image Acquisition, Processing, and Display

Figure 3:
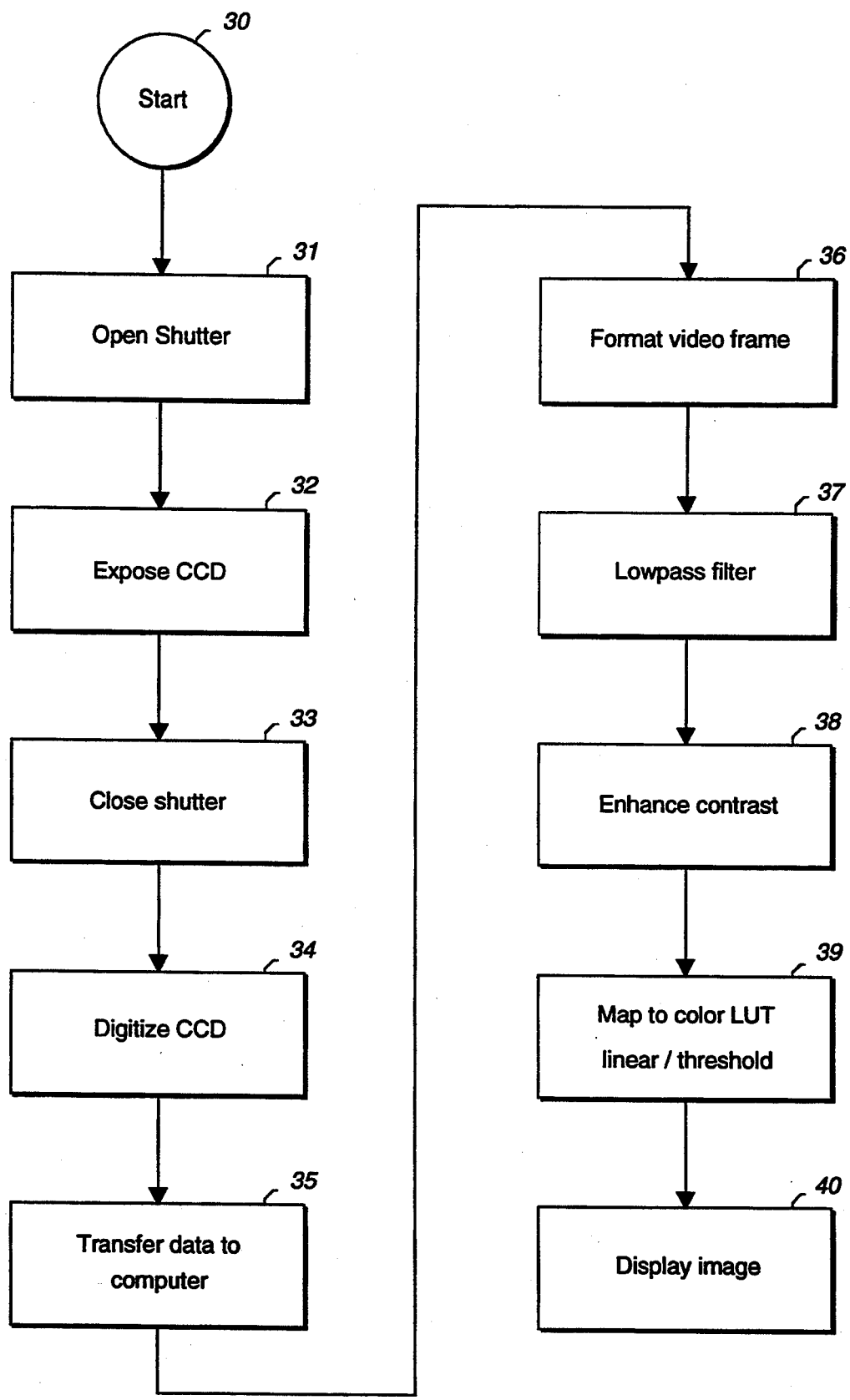
FIG. 3 is a flow chart of the image processing algorithm.

FIG. 3 is a flow chart of the image acquisition, processing, and display algorithm used in this system. In the first step in the image acquisition cycle 30, the camera controller 11 sends a command to the CCD video camera 10 to open its shutter 31. The image is then integrated on the CCD for the predetermined exposure period 32, and the shutter is closed 33. The contents of each pixel in the CCD is then sequentially read out and digitized 34 by the analog-to-digital converter in the camera controller, and the digitized data is transferred 35 to the interface board 12 in the computer 13. As the interface board receives the digitized data from the camera controller, it stores the data in main computer memory via a high-speed DMA transfer and reformats the data 36 into a video frame. When a full video frame has been received, the CSMA software lowpass-filters 37 the frame to remove high-spatial-frequency irregularities and noise caused by the fiber optic imaging system, and autoscales 38 the frame data to fill the entire 256-level (8-bit) data scale and thus enhance image contrast. The frame data is then mapped 39 into the output lookup table (LUT). The LUT can be configured either as a linear color scale with between 16 and 64 discrete colors each representing a different tissue brightness value in the surgical or endoscopic field of view, or as a threshold-level scale, with all tissue brightness values between zero and a user-selected threshold represented by one color and all tissue brightness values above the threshold and below full-scale represented by a second color. This latter display mode emphasizes hypermetabolic areas in the surgical or endoscopic field of view. Finally, the color-coded or threshold-level-coded frame is displayed 40 on an internal or external standard VGA display together with the CSMA menu commands as a 640×480 pixel image and text Windows-type display.

I claim:

1. A system for differentiating and localizing tissue in situ in the human body during a surgical procedure comprising;
   a) an imaging agent and means for administering the imaging agent to a patient, said imaging agent being transported across cell membranes with said tissue to facilitate attachment of the imaging agent to a substrate binding site of a hexokinase enzyme within the cell;
   b) illumination means for generating an illuminating light onto said tissue in a surgical field of view;
   c) optical bandpass excitation filter means disposed between said illumination means and the tissue in the surgical field of view for illuminating said tissue with a wavelength of light predetermined to excite fluorescent emission in said imaging agent;
   d) a video camera for generating video signals representing an image of said illuminated tissue;
   e) optical bandpass filter disposed between said tissue and said video camera, said optical bandpass filter for filtering said image at a wavelength of light corresponding to the emission wavelength of said imaging agent; and
   f) display means coupled to said video camera for displaying said filtered image representing the relative metabolic rates of different areas of said tissue.

2. The system defined by claim 1 wherein said imaging agent consists of a glucose analog coupled to a fluorophore such that said imaging agent is accumulated in said body tissue at a rate proportional to the glucose metabolic rate of said tissue.

3. The system defined by claim 1 further comprising video digitizing means coupled to said video camera for converting said video signals to a two-dimensional digital matrix which represents brightness of said tissue.

4. The system defined by claim 3 further comprising image formatting and processing means coupled to said video digitizing means for analyzing said two-dimensional digital matrix and for generating a color-coded or threshold-level image representing areas of differing brightness in said tissue.

5. A system for differentiating and localizing tissue in situ in the human body during an endoscopic procedure comprising:
   a) an imaging agent and means for administering the imaging agent to a patient, said imaging agent being transported across cell membranes within said tissue to facilitate attachment of the imaging agent to a substrate binding site of a hexokinase enzyme within the cell;
   b) illumination means for generating an illuminating light;
   c) endoscopic means for conveying the illuminating light to said tissue under examination via a first fiber optic bundle and for returning an image of the illuminated tissue via a second fiber optic bundle;
   d) optical bandpass excitation filter means disposed between said illumination means and said first fiber optic bundle for illuminating said tissue with a wavelength of light predetermined to excite fluorescent emission in said imaging agent;
   e) a video camera;
   f) optical bandpass filter disposed between said second fiber optic bundle and said video camera, said video camera for generating video signals representing said returned image filtered by said optical bandpass filter at a wavelength of light corresponding to the emission wavelength of said imaging agent; and
   g) display means coupled to said video camera for displaying said returned and filtered image representing the relative metabolic rates of different areas of said tissue.

6. The system defined by claim 5 wherein said imaging agent consists of a glucose analog coupled to a fluorophore such that said imaging agent is accumulated in said body tissue at a rate proportional to the glucose metabolic rate of said tissue.

7. The system defined by claim 5 further comprising video digitizing means coupled to said video camera for converting said video signals to a two-dimensional digital matrix which represents brightness of said tissue.

8. The system defined by claim 7 further comprising image formatting and processing means coupled to said video digitizing means for analyzing said two-dimensional digital matrix and for generating a color-coded or threshold-level image representing areas of differing brightness in said tissue.

9. A method for differentiating and localizing tissue in situ in the human body during a surgical procedure comprising the steps of:
   a) administering an imaging agent to a patient such that said imaging agent is transported across cell membranes within said tissue to facilitate attachment of the imaging agent to a substrate binding site of a hexokinase enzyme within the cell;
   b) generating an illuminating light;
   c) filtering said illuminating light through an optical bandpass excitation filter adapted to pass light at a wavelength predetermined to excite fluorescent emission in said imaging agent onto tissue to be examined during the surgical procedure;
   d) transmitting through an optical bandpass filter an image of said illuminated tissue at a wavelength of light corresponding to the emission wavelength of said imaging agent; and
   e) displaying said transmitted and filtered image representing the relative metabolic rates of different areas of said tissue;
   f) performing said surgical procedure by making an incision in said human body to remove said tissue being examined.

10. The method defined by claim 9 wherein said imaging agent consists of a glucose analog coupled to a fluorophore such that said imaging agent is accumulated in said body tissue at a rate proportional to the glucose metabolic rate of said tissue.

11. The method defined by claim 9 further comprising the steps of:
  a) converting said transmitted image of said illuminated tissue to a video signal:
  b) converting said video signal to a two-dimensional digital matrix which represents brightness of said tissue.

12. The method defined by claim 11 further comprising the steps of analyzing said two-dimensional digital matrix and generating a color-coded or threshold-level image representing areas of differing brightness in said tissue.

13. A method for differentiating and localizing tissue in situ in the human body during an endoscopic procedure comprising the steps of:
  a) administering an imaging agent to a patient such that said imaging agent is transported across cell membranes within said tissue to facilitate attachment of the imaging agent to a substrate binding site of a hexokinase enzyme within the cell;
  b) generating an illuminating light;
  c) filtering said illuminating light through an optical bandpass excitation filter adapted to pass light at a wavelength predetermined to excite fluorescent emission in said imaging agent onto tissue to be examined during the endoscopic procedure;
  d) returning through an optical bandpass filter an image of said illuminated tissue at a wavelength of light corresponding to the emission wavelength of said imaging agent; and
  e) displaying said returned and filtered image representing the relative metabolic rates of different areas of said tissue.

14. The method defined by claim 13 wherein said imaging agent consists of a glucose analog coupled to a fluorophore such that said imaging agent is accumulated in said body tissue at a rate proportional to the glucose metabolic rate of said tissue.

15. The method defined by claim 10 further comprising the steps of:
  a) converting said returned image of said illuminated tissue to a video signal;
  b) converting said video signal to a two-dimensional digital matrix which represents brightness of said tissue.

16. The method defined by claim 15 further comprising the steps of analyzing said two-dimensional digital matrix and generating a color-coded or threshold-level image representing areas of differing brightness in said tissue.

* * * * *